(12) United States Patent
Hodges et al.

(10) Patent No.: US 6,541,621 B1
(45) Date of Patent: Apr. 1, 2003

(54) HYPOXIA INDUCIBLE PROMOTER

(75) Inventors: Thomas K. Hodges, West Lafayette, IN (US); Enamul Huq, El Sobrante, CA (US); Anwar Hossain, Dhaka (BD)

(73) Assignee: Purdue University Research Foundation, West Lafayette, IN (US)

( * ) Notice: Subject to any disclaimer, the term of this patent is extended or adjusted under 35 U.S.C. 154(b) by 0 days.

(21) Appl. No.: 09/508,213

(22) PCT Filed: Sep. 11, 1998

(86) PCT No.: PCT/US98/18955

§ 371 (c)(1),
(2), (4) Date: Mar. 8, 2000

(87) PCT Pub. No.: WO99/13067

PCT Pub. Date: Mar. 18, 1999

Related U.S. Application Data

(60) Provisional application No. 60/058,639, filed on Sep. 12, 1997.

(51) Int. Cl.[7] .......................... C07H 21/04; C12N 15/82
(52) U.S. Cl. .................................... 536/24.1; 435/320.1
(58) Field of Search ...................... 435/320.1; 536/23.1, 536/24.1, 24.3

(56) References Cited

PUBLICATIONS

Gallie. 1998. Controlling gene expression in transgenics. Current Opinion in Plant Biology 1:166–172.*
Huq et al. 1997.GenEmbl Accession U38199. See enclosed sequence search report, Result 1.*
Chen et al. 1997.GenEmbl Accession U70541. See enclosed sequence search report, Result 2.*
Kellerman et al., "Analysis of the Primary Structure of the Power Promoter Function of a pyruvate decarboxylase Gene from *Saccharomyces Cerevisea" Nucleic Acid Research*, 14: 8963–8977, 1986.
Kelley et al. *Plant Molecular Biology*, 17: 1259–1261, 1991.
Conway et al. "Promoter and Nucleotide Sequences of the *Zymomonas mobilis* Pyruvate Decarboxylase" *Journal of Bacteriology*, 169: 949–954 1987.
de Vetten, N.C., "Transcriptional Regulation of Environmentally Inducible Genes in Plants by Evolutionary Conserved Family of G–box Binding Factors" *Int. J. Biochem.*, Sep. 1994, vol. 26, pp. 1055–1068.
Causse et al. "Saturated Molecular Map of the Rice Genome Based on an Interspecific Backross Population" *Genetics*, Dec. 1994, vol. 138, No. 4, pp. 1251–1274.

Crawford, R.M.M et al. "Oxygen Deprivation Stress in a Changing Environment" *J. Exp. Botany*, Feb. 1996, vol. 47, No. 295, pp. 145–159.
Olive et al. "The Anaerobic Responsive Element Contains Two GC–rich Sequences Essential for Binding a Nuclear Protein and Hypoxic Activation of the Maize Adh1 Promoter" *Nucleic Acids Res.*, Dec. 1991, vol. 19, pp. 7053–7060.
Rivoal et al. "Differential Induction of Pyruvate Decarboxylase Subunits and Transcripts in Anoxic Rice Seedlings." *Plant Physiology*, vol. 114, pp. 1021–1029, 1997.
Johnson et al. "Hypoxic Induction of Anoxia Tolerance in Roots of *Adh 1* Null Zea mays L."*Plant Physiology*, vol. 105, pp. 61–67, 1994.
Dolferus et al. "Differential Interactions of Promoter Elements in Stress Responses of the *Arabidopsis Adh* Gene." *Plant Physiology*, vol. 105, pp. 1075–1087, 1994.
Hossain et al. "Sequence of cDNA from *Oryza sativa* (L.) Encoding the Pyruvate Decarboxylase 1 Gene." *Plant Physiology*, vol. 106, pp. 799–800, 1994.
Setter et al. "Physiology and Genetics of Submergence Tolerance in Rice." *Annals of Botany*, vol. 79, supplement A, pp. 67–77, 1997.
Ferl and Laughner "In vivo detection of regulatory factor binding sites of *Arabidopsis thaliana Adh.*" *Plant Molecular Biology*, vol. 12, pp. 357–366, 1989.
Hossain et al. "Nucleotide Sequence of a Rice Genomic Pyruvate Decarboxylase GEne that Lacks Introns: A Pseudo– Gene?" *Plant Physiology*, vol. 106, pp. 1697–1698, 1994.
Bailey–Serres and Freeling "Hypoxic Stress–induced Changes in Ribosomes of Maize Seedling Roots." *Plant Physiology*, vol. 94, pp. 1237–1243, 1990.
Huq et al. (1995) Cloning and Sequencing of a cDNA Encoding Pyruvate Decarboxylase 2 Gene (Accession No. U27305) from Rice. *Plant Physiology* 109:722.
Huq et al. (1997) Characterization of a cDNA Encoding a Polyubiquitin Gene in Rice (Accession No. U37687). *Plant Physiology* 113: 305.

* cited by examiner

*Primary Examiner*—James Ketter
*Assistant Examiner*—Bronwen M. Loeb
(74) *Attorney, Agent, or Firm*—Barnes & Thornburg

(57) ABSTRACT

The present invention is directed to nucleic acid sequences encoding a novel regulatory element that induces a high level of expression to operably linked genes, upon exposure to hypoxic conditions. Furthermore, the regulatory element can be used to prepare an expression vector for transforming plant cells, wherein the DNA construct comprises a hypoxia inducible promoter operably linked to a gene sequence.

12 Claims, 1 Drawing Sheet

SEQUENCE LISTING

<160> NUMBER OF SEQ ID NOS: 3

<210> SEQ ID NO 1
<211> LENGTH: 5526
<212> TYPE: DNA
<213> ORGANISM: Oryza sativa

<400> SEQUENCE: 1

```
atgcataaaa cagtggtttc tcttagaaaa aaaaggaaaa ttggaagcat gttactataa      60
ttttataaaa tttaaaatat gtcattttga tccatatgtc attgactcat gtagatttta     120
catgttattg agatacatat ggcatatctc aaactttaca aaattataat ggtatggttt     180
caaattaaaa aaaaacgtgg tgacagtgag cggtgaagaa ggtgagtcgt caacgacagg     240
acgaggttaa ttgtcagatg gcagaaccac tagaaacaag aaaaatgaca cggcacggag     300
gcaccaataa aatgaaaatg ttaaaggaga gaaaaggtg agagcgcacg aaaggttcat      360
ggtcttacga tatagtaatt ggcaacctaa taaggcagtg acacctaggc atatttacta     420
tcattttatt atcaaattat ttaatttgta aaataaaatt gttctcaaac atctaaaaag     480
ttggtattag aaataagtaa aaagttcgta ttatctaaaa agtaaacaat agtaatcggc     540
aaagagagac aaggaagtgt aagtcaatta ctccattcat ctcaaaatac agtaacttat     600
agcctacttc ataagttagt ggtggtggtg atagactcgt cgtctcccct gttaatgtta     660
atgttagtat tatgaatttg aagattttg ttccaataat aacattttt tcctaactaa      720 ccatttgaaa taaagtggtg gatattattc gatcatatga aatttctatg gaatgcctaa     780
attttataga aaatttaaca cgaggtcctc catggaagtt ccctttgagt atacctaaac     840
accattttta tattttcatg tgttttacaa ttgaaaacgt ttgagaaatt ccactacaaa     900
```

-continued

| | |
|---|---|
| cgtacgcagg tttcaaaacc attgttcatg agaatgatat gtgttaccag gacctacata | 960 |
| ccaatgacac ataataatat ctttcaactc catgatttt acaacaacac taggcaaatc | 1020 |
| gaccatttac aatcctgtaa aaaaaatatg tttatcttac ttttttttaat tatctcaatc | 1080 |
| ctgcaatttt tcgcccttca tctttctacc caaaaaaaaa agatttgatt tgattaaatt | 1140 |
| tgtgcactac atccgtcaga gcaagtttaa tagtatagcc cactacaagc tccaattcac | 1200 |
| ctgtaaccaa tcgaataacc aattcataca atagttgctt actatattat taatatatgg | 1260 |
| tccacctgtc atacacacat catgtcttgg agtccgcgtt gcagctgcct acagatctac | 1320 |
| agcccgcttc tcttctctct tatcttttat ctcattaaaa tatatttata gctggctaag | 1380 |
| ggcacccaca attgttatct ataggctctc tacaagagat ccatgtcaac atattttcct | 1440 |
| atttagaaga tattaaatga agagagagag caaagctatc tactaactta gagatagtct | 1500 |
| atagagaaaa acgagacaag gcatgagaga gctatagata cctatgtaga catactattg | 1560 |
| aggtggttta ctattaatct agtctattac tgagatgtac atatttatat agaaacacat | 1620 |
| taatttacca ttacaggtgc tctaatagtc tgctattata tgtgctctca tgcgtcatcc | 1680 |
| atggtagcgg atagaatgca gaagtctacg cgccgtacgc ctcctgtgcg ggatcaggat | 1740 |
| cgtcaggcga gccacgtgac cacgtctgat gtggcgggct ggagctacta gctacggtgc | 1800 |
| tttctgccgc cgcctacacc tttgccacgc agcccaaaac gagtccacct tgcgcagcaa | 1860 |
| acaaaaccaa aaccgccgcc ttgcgtcgca aaaccagaaa acaccaccgc cgccgccgca | 1920 |
| ccgcacacgc ccccgccttc ccctgatcgc gacgaaacca tttccgtcgc gaatctggat | 1980 |
| actggagaga ccgcgagtca ccgacgcgcg cccaagccac gctgcccac cgagcagatc | 2040 |
| gcatcgcccg cgagatcacc ggcgtgccgg cctcccccac cccaatctcg cccgtggttt | 2100 |
| tcgtcgaaag gaatacaggt ttttgcacgg aagcccccgg gtttccacac caattctcga | 2160 |
| tctgcccccg cctccatggt ataaaacgag acacattcct ccccaccgct gaatccatcc | 2220 |
| atccaccgaa ccatacccaa caagcgtcaa atcgcgtcaa agccaaaaac ctcatacaag | 2280 |
| tccaggaatc tgtaatatat tccgagactt ttacacgcat tccagtcatc actagtgtag | 2340 |
| cggttgctgc ttcttccccg gggaggttta tcggatcttg atggagaccc atatcggatc | 2400 |
| cgtggacggg gcggcggcgg cggcggacaa cggcgcggtg gggtgcccgg cgtcggcggt | 2460 |
| ggggtgcccg atgacctcgg cgcgccccgg cgtgtcggcc cggcgaggcg tcgctgggac | 2520 |
| ggcacctggc gaggcggctg gtgcaggtgg gcgtcagcga cgtgttcgcg tgcccgggga | 2580 |
| cttcaacctc acgctgctcg accacctgat cgccgagccc ggcctgctcg tcggctgctg | 2640 |
| taacgagctc aacgccgggt acgccgccga cggctacgcg cggtcgcggg gcgtcggcgc | 2700 |
| ctgcgccgtc acgttcaccg tcggcggact cagcgtgctc aacgccatcg ccggcgcgta | 2760 |
| cagcgagaac ctgccggtca tctgcatcgc cggagggccg aactccaacg actacggcac | 2820 |
| taaccgcatc ctccaccaca ccatcggcct cccggacttc tcccaggagc tccgctgctt | 2880 |
| ccagaccgtc acttgcaccc aggtacgtgt cccccctct gctcctcctc ggatttcccc | 2940 |
| ctaatttctt gggttgcaga tttggttgga tcgatcgatg gtttgctaat gtttgtggat | 3000 |
| tcaggcggtg gtgaccaatc tggaggatgc gcacgagcag atcgacaccg ccatcgcgac | 3060 |
| ggcgctgcgg gagagcaagc ctgtgtacct cagcatcagc tgcaatctcc cagggctgcc | 3120 |
| tcaccccacg tttagccgcg accccgtccc cttcttcctc gccccaggt accctctcc | 3180 |
| gttttatcat gaagcttatc ccataatcta ccaatttgt catgccatgt ctcgattcaa | 3240 |
| gagagtagga tttatttac cccaaaaagg acgcctggtt gaattataag tattgagatc | 3300 |

-continued

```
gtgcatattt gatacagtac cggaagttgt ctgatgattt caatatgttg taatatttca    3360
cttcagttcg atgctataag attggttgta ccaatgcatt tcagatttt gattcgatgc     3420 tatgaaattg gttgtaccat tgcatttcag attttcagtt tgtctgatga aattgtggca    3480
ttgcaggttg agtaacaaga tgggtctgga ggctgcggtg gaggccactg tcgagttcct    3540
gaacaaggcg gtgaagccgg tgctcgttgg cggcccaag ctgcgtgtgg caaaggcagg     3600
gaaggccttc gtcgaccttg ttgatgccag tggctacccc tacgcggtga tgccgtcggc    3660
caaggggctc gtgccggaga cgcaccccca cttcatcggc acctactggg gtgcggtcag    3720
cacggccttc tgtgccgaga tcgtcgagtc ggccgacgcc tacctcttcg cagggccaat    3780
cttcaatgac tacagctctg tcggctactc cttcctcctc aagaaggaca aggccataat    3840
tgtgcaaccg agcgtgtca tcgtcgggaa tggcccggcg tttgggtgcg tcatgatgaa     3900
ggagttctta tctgagctgg ctaagcgcgt caacaagaac accactgctt acgagaacta    3960
caagaggatc ttcgtcctga gggccagcgc tggagaggag ccgaatgagc cgctgcgcgt    4020
caatgtgctc ttcaagcacg tccagaagat gctgaacagt gacagtgctg tgattgccga    4080
gactggtgac tcctggttca attgccagaa gctgaagctc cctgagggct gcgggtgagc    4140
attctgaaac ttgctacaac cctgttgtga atggttttac aatgttcttg gtgaatatac    4200
tgagtggttt attgcatgct gcaggtatga attccaaatg cagtatggtt ccattggatg    4260
gtcagtgggt gcattgctcg gatatgctca gggcgctaag acaagcgtg tgattgcctg     4320 tattggtgat gggagtttcc aggtgaagca ccgtgatcac ttgatctttt gatcagatat    4380
gttgctaata tgatggcatg ttactgatgt gtgatcgtgg taatttcctg caggtgacgg    4440
cacaggatgt gtcaacaatg attcgctgtg cacagaacag cataatcttc ctgatcaaca    4500
acggcgggta caccattgag gtggagatcc atgacggtcc atacaacgtc atcaagaact    4560
ggaactacac tggtcttgtg gatgccatcc acaatggaga gggcaaatgc tggacttcta    4620
aggtatgcta actcttcgat cacctgcat tcaccacacg aggcttagac cgcagatgct      4680
cctatatctg aggaactgtt gctgatggtt gccatgatgt acattgcgca ggtgaagtgc    4740
gaggaggagc tgacggaggc gatcgggatg gcgctggggg agaagaagga ctgcctgtgc    4800
ttcattgagg tgatcgcgca caaggacgac accagcaaag agctgctgga atgggatcg     4860 aggtttctg ctgccaactc caggccacca aatcctcagt agaaacttt agtacttagt       4920 tgcaagctgg gctcaatcat aataatgtaa acactttgcc cttcagttat gttccttgtg    4980
tccattccct cgggtttctg ttcttccagt ttcggtagct ctgtatctac ttgtgaacat    5040
ctgtttctcc aatcaaatgc tacgagggtt atgagaggtt ttcagcttgc atccaactgt    5100
ttgattttgt gttgccatct gctacccggc acttggtaac gatttgatga gagcatggcc    5160
ggccagtgaa tcctgtgatc tgtgcgagat ccgtcacttg gaggcaggct actattgcat    5220
ggtcctcctc ccgtgagccg ttacttgtct ctgtctgcaa gaaaatggcg atgaaattca    5280
gaagcgctag atcggtgtca acagggcaat aatctgtac ttcctccgtc tcaaaataaa     5340
tatagtttta cactattcac gtttacattt gaccgtttgt cttatttaaa tttatttta    5400 tgattagtat tttattact attaggacta aatatttttt aattttcat aaattttta      5460 aataagacga tggcaaatgt taggcacgaa tatcataatg tagaagatat tcgcgatatt    5520
agagag                                                               5526
```

<210> SEQ ID NO 2

<211> LENGTH: 2380
<212> TYPE: DNA
<213> ORGANISM: Oryza sativa

<400> SEQUENCE: 2

```
atgcataaaa cagtggtttc tcttagaaaa aaaggaaaaa ttggaagcat gttactataa      60
ttttataaaa tttaaaatat gtcattttga tccatatgtc attgactcat gtagatttta     120
catgttattg agatacatat ggcatatctc aaactttaca aaattataat ggtatggttt     180
caaattaaaa aaaacgtggg tgacagtgag cggtgaagaa ggtgagtcgt caacgacagg     240
acgaggttaa ttgtcagatg cagaaccac tagaaacaag aaaaatgaca cggcacggag      300
gcaccaataa aatgaaaatg ttaaaggaga aaaaaggtg agagcgcacg aaaggttcat      360
ggtcttacga tatagtaatt ggcaacctaa taaggcagtg acacctaggc atatttacta     420
tcatttatt atcaaattat ttaatttgta aaataaaatt gttctcaaac atctaaaaag      480
ttggtattag aaataagtaa aaagttcgta ttatctaaaa agtaaacaat agtaatcggc     540
aaagagagac aaggaagtgt aagtcaatta ctccattcat ctcaaaatac agtaacttat     600
agcctacttc ataagttagt ggtggtggtg atagactcgt cgtctcccct gttaatgtta     660
atgttagtat tatgaatttg aagatttttg ttccaataat aacattttt tcctaactaa      720
ccatttgaaa taaagtggtg gatattattc gatcatatga aatttctatg gaatgcctaa     780
attttataga aaatttaaca cgaggtcctc catggaagtt cccttttgagt atacctaaac    840
accattttta tattttcatg tgttttacaa ttgaaaacgt ttgagaaatt ccactacaaa     900
cgtacgcagg tttcaaaacc attgttcatg agaatgatat gtgttaccag gacctacata     960
ccaatgacac ataataatat ctttcaactc catgattttt acaacaacac taggcaaatc    1020
gaccatttac aatcctgtaa aaaaaatatg tttatcttac ttttttttaat tatctcaatc    1080
ctgcaatttt tcgcccttca tctttctacc caaaaaaaaa agatttgatt tgattaaatt     1140
tgtgcactac atccgtcaga gcaagtttaa tagtatagcc cactacaagc tccaattcac    1200
ctgtaaccaa tcgaataacc aattcataca atagttgctt actatattat taatatatgg    1260
tccacctgtc atacacacat catgtcttgg agtccgcgtt gcagctgcct acagatctac    1320
agcccgcttc tcttctctct tatctttat ctcattaaaa tatatttata gctggctaag     1380
ggcacccaca attgttatct ataggctctc tacaagagat ccatgtcaac atattttcct    1440
atttagaaga tattaaatga agagagagag caaagctatc tactaactta gagatagtct    1500
atagagaaaa acgagacaag gcatgagaga gctatagata cctatgtaga catactattg    1560
aggtggttta ctattaatct agtctattac tgagatgtac atatttatat agaaacacat    1620
taatttacca ttacaggtgc tctaatagtc tgctattata tgtgctctca tgcgtcatcc    1680
atggtagcgg atagaatgca gaagtctacg cgccgtacgc ctcctgtgcg ggatcaggat    1740
cgtcaggcga gccacgtgac cacgtctgat gtggcgggct ggagctacta gctacggtgc    1800
tttctgccgc cgcctacacc tttgccacgc agcccaaaac gagtccacct tgcgcagcaa    1860
acaaaaccaa aaccgccgcc ttgcgtcgca aaaccagaaa acaccaccgc cgccgccgca    1920
ccgcacacgc cccgccttc ccctgatcgc gacgaaacca tttccgtcgc gaatctggat     1980
actggagaga ccgcgagtca ccgacgcgcg cccaagccac gctgccccac cgagcagatc    2040
gcatcgcccg cgagatcacc ggcgtgccgg cctccccac cccaatctcg cccgtggttt     2100
tcgtcgaaag gaatacaggt ttttgcacgg aagcccccgg gttccacac caattctcga     2160
tctgcccccg cctccatggt ataaaacgag acacattcct ccccaccgct gaatccatcc    2220
```

-continued

```
atccaccgaa ccatacccaa caagcgtcaa atcgcgtcaa agccaaaaac ctcatacaag    2280
tccaggaatc tgtaatatat tccgagactt ttacacgcat tccagtcatc actagtgtag    2340
cggttgctgc ttcttccccg gggaggttta tcggatcttg                          2380
```

<210> SEQ ID NO 3
<211> LENGTH: 604
<212> TYPE: PRT
<213> ORGANISM: Oryza sativa

<400> SEQUENCE: 3

```
Met Glu Thr His Ile Gly Ser Val Asp Gly Ala Ala Ala Ala Asp
 1               5                  10                  15

Asn Gly Ala Val Gly Cys Pro Ala Ser Ala Val Gly Cys Pro Met Thr
                20                  25                  30

Ser Ala Arg Pro Gly Val Ser Ala Arg Arg Gly Val Ala Gly Thr Ala
            35                  40                  45

Pro Gly Glu Ala Ala Gly Ala Gly Gly Arg Gln Arg Arg Val Arg Val
        50                  55                  60

Pro Gly Asp Phe Asn Leu Thr Leu Leu Asp His Leu Ile Ala Glu Pro
65                  70                  75                  80

Gly Leu Leu Val Gly Cys Cys Asn Glu Leu Asn Ala Gly Tyr Ala Ala
                85                  90                  95

Asp Gly Tyr Ala Arg Ser Arg Gly Val Gly Ala Cys Ala Val Thr Phe
            100                 105                 110

Thr Val Gly Gly Leu Ser Val Leu Asn Ala Ile Ala Gly Ala Tyr Ser
        115                 120                 125

Glu Asn Leu Pro Val Ile Cys Ile Ala Gly Gly Pro Asn Ser Asn Asp
    130                 135                 140

Tyr Gly Thr Asn Arg Ile Leu His His Thr Ile Gly Leu Pro Asp Phe
145                 150                 155                 160

Ser Gln Glu Leu Arg Cys Phe Gln Thr Val Thr Cys Thr Gln Ala Val
                165                 170                 175

Val Thr Asn Leu Glu Asp Ala His Glu Gln Ile Asp Thr Ala Ile Ala
            180                 185                 190

Thr Ala Leu Arg Glu Ser Lys Pro Val Tyr Leu Ser Ile Ser Cys Asn
        195                 200                 205

Leu Pro Gly Leu Pro His Pro Thr Phe Ser Arg Asp Pro Val Pro Phe
    210                 215                 220

Phe Leu Ala Pro Arg Leu Ser Asn Lys Met Gly Leu Glu Ala Ala Val
225                 230                 235                 240

Glu Ala Thr Val Glu Phe Leu Asn Lys Ala Val Lys Pro Val Leu Val
                245                 250                 255

Gly Gly Pro Lys Leu Arg Val Ala Lys Ala Gly Lys Ala Phe Val Asp
            260                 265                 270

Leu Val Asp Ala Ser Gly Tyr Pro Tyr Ala Val Met Pro Ser Ala Lys
        275                 280                 285

Gly Leu Val Pro Glu Thr His Pro His Phe Ile Gly Thr Tyr Trp Gly
    290                 295                 300

Ala Val Ser Thr Ala Phe Cys Ala Glu Ile Val Glu Ser Ala Asp Ala
305                 310                 315                 320

Tyr Leu Phe Ala Gly Pro Ile Phe Asn Asp Tyr Ser Ser Val Gly Tyr
                325                 330                 335

Ser Phe Leu Leu Lys Lys Asp Lys Ala Ile Ile Val Gln Pro Glu Arg
```

-continued

|  | 340 |  |  |  | 345 |  |  |  | 350 |  |  |  |
|---|---|---|---|---|---|---|---|---|---|---|---|---|
| Val | Ile | Val | Gly | Asn | Gly | Pro | Ala | Phe | Gly | Cys | Val | Met | Met | Lys | Glu |
|  |  | 355 |  |  |  | 360 |  |  |  | 365 |  |  |

```
Val Ile Val Gly Asn Gly Pro Ala Phe Gly Cys Val Met Met Lys Glu
        355                 360                 365

Phe Leu Ser Glu Leu Ala Lys Arg Val Asn Lys Asn Thr Thr Ala Tyr
    370                 375                 380

Glu Asn Tyr Lys Arg Ile Phe Val Leu Arg Ala Ser Ala Gly Glu Glu
385                     390                 395                 400

Pro Asn Glu Pro Leu Arg Val Asn Val Leu Phe Lys His Val Gln Lys
                405                 410                 415

Met Leu Asn Ser Asp Ser Ala Val Ile Ala Glu Thr Gly Asp Ser Trp
                420                 425                 430

Phe Asn Cys Gln Lys Leu Lys Leu Pro Glu Gly Cys Gly Tyr Glu Phe
        435                 440                 445

Gln Met Gln Tyr Gly Ser Ile Gly Trp Ser Val Gly Ala Leu Leu Gly
    450                 455                 460

Tyr Ala Gln Gly Ala Lys Asp Lys Arg Val Ile Ala Cys Ile Gly Asp
465                 470                 475                 480

Gly Ser Phe Gln Val Thr Ala Gln Asp Val Ser Thr Met Ile Arg Cys
            485                 490                 495

Ala Gln Asn Ser Ile Ile Phe Leu Ile Asn Asn Gly Gly Tyr Thr Ile
                500                 505                 510

Glu Val Glu Ile His Asp Gly Pro Tyr Asn Val Ile Lys Asn Trp Asn
        515                 520                 525

Tyr Thr Gly Leu Val Asp Ala Ile His Asn Gly Glu Gly Lys Cys Trp
    530                 535                 540

Thr Ser Lys Val Lys Cys Glu Glu Glu Leu Thr Glu Ala Ile Gly Met
545                 550                 555                 560

Ala Leu Gly Glu Lys Lys Asp Cys Leu Cys Phe Ile Glu Val Ile Ala
                565                 570                 575

His Lys Asp Asp Thr Ser Lys Glu Leu Leu Glu Trp Gly Ser Arg Val
                580                 585                 590

Ser Ala Ala Asn Ser Arg Pro Pro Asn Pro Gln Glx
        595                 600
```

HYPOXIA INDUCIBLE PROMOTER

CROSS-REFERENCE TO RELATED APPLICATIONS

This application is a U.S. national application of international application serial No. PCT/US98/18955 filed Sep. 11, 1998, which claims priority to U.S. provisional application serial No. 60/058,639 filed Sep. 12, 1997.

FIELD OF THE INVENTION

The present invention is directed to nucleic acid sequences encoding a novel regulatory element that induces a high level of expression to operably linked genes, upon exposure to anaerobic conditions.

INTRODUCTION

Pyruvate decarboxylase (PDC) is a critical enzyme in the anaerobic-specific fermentation pathway. PDC nonoxidatively decarboxylates pyruvate to acetaldehyde which is very toxic to plants. Acetaldehyde is then reduced to ethanol by alcohol dehydrogenase (ADH), regenerating NAD+ which is then utilized in the glycolytic pathway to maintain carbon flow through this pathway under anaerobic conditions. Switching energy production from aerobic glycolysis to anaerobic fermentation is one of the major metabolic adaptations plants undertake when they are submerged or confronted with a lack of oxygen. The importance of increased rates of alcoholic fermentation (AF) under anaerobic conditions was demonstrated by several experimental observations:

(i) enzymes for AF often increase;
(ii) mutants without ADH die more rapidly during anoxia;
(iii) increased tolerance to anoxia comes from hypoxic pretreatments and presumably induction of enzymes of AF;
(iv) high sugar supply increases survival—presumably due to increased rates of AF; and
(v) rates of AF are related to tolerance of several species to waterlogging or flooding. It has also been suggested that the rate of AF is limited by PDC.

The role of ADH in metabolism and survival of anoxic maize root tips has been investigated by comparing the ethanol production of isogenic lines differing in ADH activity over a ~200-fold range. It was concluded that ADH activity in wild-type maize root tips was not a limiting factor for energy production via fermentation and did not determine viability under anoxia. This conclusion was further supported by additional experiments showing that 70% of the hypoxia acclimated root tips of Adh1 null maize survived up to 24 hours of anoxia, whereas only 10% of the unacclimated root tips survived for 6 hours of anoxia. It was also concluded that the high levels of ADH activity inducible in acclimated wild-type maize root tips are in excess of that required to increase rates of fermentation. Thus, PDC, being the first enzyme in the AF pathway, may play a key regulatory role in energy production in cells exposed to hypoxic conditions.

It has been reported that over-expression of a pdc gene from *Zymonionas mobilis* in tobacco cells results in higher levels of acetaldehyde and ethanol formation, supporting the idea that PDC is likely to be the key regulator of anaerobic metabolism. Unfortunately, the measurements made in this study were only up to 24 hours after anoxia treatment which did not allow for an evaluation of tolerance under long-term anoxia. Moreover, rice might have different mechanisms of submergence tolerance than tobacco as evidenced by the fact that it is relatively more tolerant among other monocots.

Genes encoding PDC have been cloned and characterized from maize (Kelley et al., Plant Mol. Biol. 17: 1259–1261, 1991), yeast (Kellerman et al., Nucl. Acids Res. 14: 8963–8977, 1986), and bacteria (Conway et al., J. Bact. 169: 949–954, 1987). Recently, the isolation and characterization of two pdc cDNA's and two genomic clones from rice have been reported, and an additional partial cDNA clone named pdc4 has also been reported. The present invention is directed to the characterization of the pdc2 gene and the relative induction of the pdc1 and pdc2 genes over time in both shoots and roots under anaerobic conditions. The present disclosure also presents the map locations of these genes on rice chromosomes and predicts the locations of orthologous loci on maize, oat, and Triticeae chromosomes. The evolutionary relationships among pdc genes from rice, maize, yeast, and bacteria are also discussed.

DETAILED DESCRIPTION OF THE INVENTION

Figure 1:
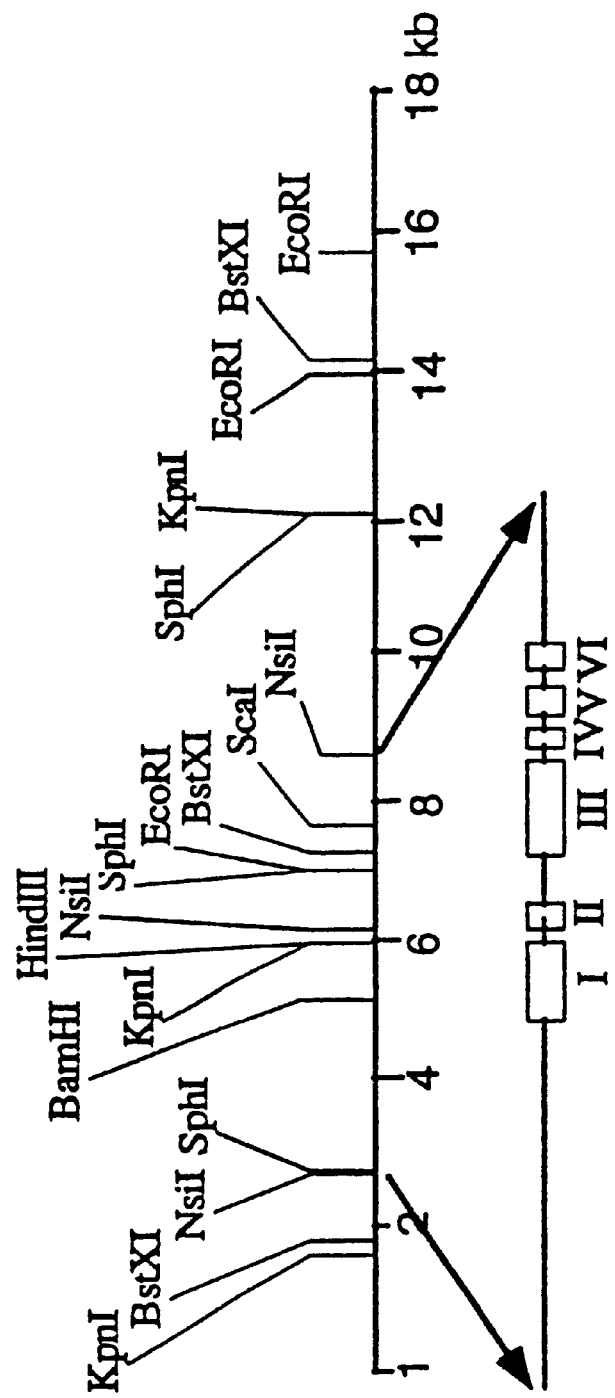
FIG. 1 is restriction map of the lambda clone 2B containing the pdc2 gene. The 5.9 kb region which contains the gene and about 2.38 kb 5' upstream region is shown in larger scale. The empty boxes are the exons and the lines in between the boxes are the introns.). The location of restriction enzyme sites is also shown.

The present invention describes the isolation and purification of a new plant DNA sequence capable of regulating the expression of foreign genes in cells such that the genes are expressed upon exposure of the cells to anaerobic conditions.

The terms "gene" and "gene sequences" as used herein refer to nucleic acid sequences that encode a polypeptide. A gene must be operably linked to a promoter to express the encoded polypeptide in a cell.

The term "expression" refers to the biosynthesis of a gene product. For example, in the case of a structural gene, expression involves the transcription of the structural gene into messenger RNA and the translation of messenger RNA into one or more polypeptides.

An expression vector is a DNA molecule comprising the regulatory elements necessary for expressing a gene in a host cell. Typically gene expression is placed under the control of certain regulatory elements including constitutive or inducible promoters, tissue-specific regulatory elements, and enhancer elements. When the transcription of a DNA sequence is controlled by a regulatory element, that sequence is said to be "operably linked to" the regulatory element. Expression vectors typically include eukaryotic and/or bacterial selectable markers that allow for selection of cells containing the expression vector.

An exogenous DNA sequence refers to a DNA sequence that has been introduced into a host cell from an external source. A transgenic plant is a plant having one or more plant cells that contain an exogenous DNA sequence. The term stably transformed refers to a transformed cell or plant that is capable of transmitting an exogenous DNA sequence to its progeny. Typically a stably transformed host has the exogenous DNA sequence integrated into its genome.

A promoter is a DNA sequence that comprises all the regulatory nucleic acid sequences necessary for expression of an operably linked gene. Promoters can be either constitutive or inducible. A constitutive promoter controls transcription of a gene at a constant rate during the life of a cell, whereas an inducible promoter's activity fluctuates as determined by the presence (or absence) of a specific inducer, such as the presence (or absence) of an environmental factor. A hypoxia inducible promoter is a promoter that increases expression of operably linked genes upon exposure of cells carrying such a gene construct to hypoxic conditions.

A core promoter contains the essential nucleotide sequences for promoter function, including the TATA box and start of transcription. By this definition, a core promoter may or may not have detectible activity in the absence of specific sequences that may enhance the activity or confer tissue specific activity.

A visible marker is defined herein as including any gene that encodes a product that produces a phenotypic trait to the host cell or organism.

A selectable marker is defined herein as including any nucleic acid sequence or gene product that can be selected for after introduction into a cell. The selectable marker facilitates the identification of transformants.

A polylinker is a DNA sequence that contains multiple endonuclease restriction enzyme identification sequences in close proximity of one another.

The present invention is directed to an inducible promoter that expresses an operably linked gene sequence upon exposure of a cell containing such nucleic acid sequences to hypoxic conditions. In accordance with one embodiment, the inducible promoter comprises the regulatory elements of SEQ ID NO: 2. The entire nucleic acid sequence of SEQ ID No. 2 is as follows:

```
atgcataaaa cagtggtttc tcttagaaaa aaaaggaaaa ttggaagcat gttactataa tttttataaaa tttaaaatat gtcattttga tccatatgtc attgactcat gtagatttta catgttattg agatacatat ggcatatctc aaactttaca aaattataat ggtatggttt caaattaaaa aaaaacgtgg tgacagtgag cggtgaagaa ggtgagtcgt caacgacagg acgaggttaa ttgtcagatg gcagaaccac tagaaacaag aaaaatgaca cggcacggag gcaccaataa aatgaaaatg ttaaaggaga gaaaaaggtg agagcgcacg aaaggttcat ggtcttacga tatagtaatt ggcaacctaa taaggcagtg acacctaggc atatttacta tcattttatt atcaaattat ttaatttgta aaataaaatt gttctcaaac atctaaaaag ttggtattag aaataagtaa aaagttcgta ttatctaaaa agtaaacaat agtaatcggc aaagagagac aaggaagtgt aagtcaatta ctccattcat ctcaaaatac agtaacttat agcctacttc ataagttagt ggtggtggtg atagactcgt cgtctcccct gttaatgtta atgttagtat tatgaatttg aagattttg ttccaataat aacattttt tcctaactaa ccatttgaaa taaagtggtg gatattattc gatcatatga aatttctatg gaatgcctaa attttataga aaatttaaca cgaggtcctc catggaagtt ccctttgagt atacctaaac accatttta tattttcatg tgttttacaa ttgaaaacgt ttgagaaatt ccactacaaa cgtacgcagg tttcaaaacc attgttcatg agaatgatat gtgttaccag gacctacata ccaatgacac ataataatat ctttcaactc catgattttt acaacaacac taggcaaatc gaccatttac aatcctgtaa aaaaaatatg tttatcttac ttttttttaat tatctcaatc ctgcaatttt tcgcccttca tctttctacc caaaaaaaaa agatttgatt tgattaaatt tgtgcactac atccgtcaga gcaagtttaa tagtatagcc cactacaagc tccaattcac ctgtaaccaa tcgaataacc aattcataca atagttgctt actatattat taatatatgg tccacctgtc atacacacat catgtcttgg agtccgcgtt gcagctgcct acagatctac agcccgcttc tcttctctct tatcttttat ctcattaaaa tatatttata gctggctaag ggcacccaca attgttatct ataggctctc tacaagagat ccatgtcaac atattttcct atttagaaga tattaaatga agagagagag caaagctatc tactaactta gagatagtct atagagaaaa acgagacaag gcatgagaga gctatagata cctatgtaga catactattg aggtggttta ctattaatct agtctattac tgagatgtac atatttatat agaaacacat taatttacca ttacaggtgc tctaatagtc tgctattata tgtgctctca tgcgtcatcc atggtagcgg atagaatgca gaagtctacg cgccgtacgc ctcctgtgcg ggatcaggat
```

```
cgtcaggcga gccacgtgac cacgtctgat gtggcgggct ggagctacta gctacggtgc tttctgccgc cgcctacacc tttgccacgc agcccaaaac gagtccacct tgcgcagcaa acaaaaccaa aaccgccgcc ttgcgtcgca aaaccagaaa acaccaccgc cgccgccgca ccgcacacgc ccccgccttc ccctgatcgc gacgaaacca tttccgtcgc gaatctggat actggagaga ccgcgagtca ccgacgcgcg cccaagccac gctgcccccac cgagcagatc gcatcgcccg cgagatcacc ggcgtgccgg cctcccccac cccaatctcg cccgtggttt tcgtcgaaag gaatacaggt ttttgcacgg aagcccccgg gtttccacac caattctcga tctgcccccg cctccatggt ataaaacgag acacattcct ccccaccgct gaatccatcc atccaccgaa ccatacccaa caagcgtcaa atcgcgtcaa agccaaaaac ctcatacaag tccaggaatc tgtaatatat tccgagactt ttacacgcat tccagtcatc actagtgtag cggttgctgc ttcttccccg gggaggttta tcggatcttg
```

One embodiment of the present invention is directed to a polynucleotide sequence having a 20 base pair nucleotide portion identical in sequence to a consecutive 20 base pair portion of the sequence as set forth in SEQ ID NO: 2. Such a sequence can be used as a probe to isolate hypoxia inducible promotors of other genes. The sequence set forth in SEQ ID NO: 2 can also be used as a hypoxia inducible promoter to regulate the expression of operably linked genes. The presumptive TATA box of this promoter is from nucleotides 2180 to 2186. A G-box-like sequences is present at nucleotides 1752 to 1759.

The promoter of SEQ ID NO: 2 was isolated from the rice pdc2 gene. The entire sequence of the rice pdc2 gene is represented by SEQ ID NO: 1, as follows:

```
atgcataaaa cagtggtttc tcttagaaaa aaaaggaaaa ttggaagcat gttactataa ttttataaaa tttaaaatat gtcattttga tccatatgtc attgactcat gtagatttta catgttattg agatacatat ggcatatctc aactttaca aaattataat ggtatggttt caaattaaaa aaaacgtgg tgacagtgag cggtgaagaa ggtgagtcgt caacgacagg acgaggttaa ttgtcagatg gcagaaccac tagaaacaag aaaaatgaca cggcacggag gcaccaataa aatgaaaatg ttaaaggaga gaaaaaggtg agagcgcacg aaaggttcat ggtcttacga tatagtaatt ggcaacctaa taaggcagtg acacctaggc atatttacta tcattttatt atcaaattat ttaatttgta aaataaaatt gttctcaaac atctaaaaag ttggtattag aaataagtaa aaagttcgta ttatctaaaa agtaaacaat agtaatcggc aaagagagac aaggaagtgt aagtcaatta ctccattcat ctcaaaatac agtaacttat agcctacttc ataagttagt ggtggtggtg atagactcgt cgtctcccct gttaatgtta atgttagtat tatgaatttg aagattttg ttccaataat aacatttttt tcctaactaa ccatttgaaa taaagtggtg gatattattc gatcatatga aatttctatg gaatgcctaa attttataga aaatttaaca cgaggtcctc catggaagtt ccctttgagt atacctaaac accattttta tattttcatg tgtttacaa ttgaaaacgt ttgagaaatt ccactacaaa cgtacgcagg tttcaaaacc attgttcatg agaatgatat gtgttaccag gacctacata ccaatgacac ataataatat ctttcaactc catgattttt acaacaaca& taggcaaatc gaccatttac aatcctgtaa aaaaaatatg tttatcttac ttttttttaat tatctcaatc ctgcaattttt tcgcccttca tctttctacc caaaaaaaaa agatttgatt tgattaaatt tgtgcactac atccgtcaga gcaagtttaa tagtatagcc cactacaagc tccaattcac ctgtaaccaa tcgaataacc aattcataca atagttgctt actatattat taatatatgg tccacctgtc atacacacat catgtcttgg agtccgcgtt gcagctgcct acagatctac
```

-continued

```
agcccgcttc tcttctctct tatcttttat ctcattaaaa tatatttata gctggctaag ggcacccaca attgttatct ataggctctc tacaagagat ccatgtcaac atattttcct atttagaaga tattaaatga agagagagag caaagctatc tactaactta gagatagtct atagagaaaa acgagacaag gcatgagaga gctatagata cctatgtaga catactattg aggtggttta ctattaatct agtctattac tgagatgtac atatttatat agaaacacat taatttacca ttacaggtgc tctaatagtc tgctattata tgtgctctca tgcgtcatcc atggtagcgg atagaatgca gaagtctacg cgccgtacgc ctcctgtgcg ggatcaggat cgtcaggcga gccacgtgac cacgtctgat gtggcgggct ggagctacta gctacggtgc tttctgccgc cgcctacacc tttgccacgc agcccaaaac gagtccacct tgcgcagcaa acaaaaccaa aaccgccgcc ttgcgtcgca aaaccagaaa acaccaccgc cgccgccgca ccgcacacgc ccccgccttc ccctgatcgc gacgaaacca tttccgtcgc gaatctggat actggagaga ccgcgagtca ccgacgcgcg cccaagccac gctgcccac cgagcagatc gcatcgcccg cgagatcacc ggcgtgccgg cctcccccac cccaatctcg cccgtggttt tcgtcgaaag gaatacaggt ttttgcacgg aagcccccgg gtttccacac caattctcga tctgcccccg cctccatggt ataaaacgag acacattcct ccccaccgct gaatccatcc atccaccgaa ccatacccaa caagcgtcaa atcgcgtcaa agccaaaaac ctcatacaag tccaggaatc tgtaatatat tccgagactt ttacacgcat tccagtcatc actagtgtag cggttgctgc ttcttccccg gggaggttta tcggatcttg atggagaccc atatcggatc cgtggacggg gcggcggcgg cggcggacaa cggcgcggtg gggtgcccgg cgtcggcggt ggggtgcccg atgacctcgg cgcgccccgg cgtgtcggcc cggcgaggcg tcgctgggac ggcacctggc gaggcggctg gtgcaggtgg gcgtcagcga cgtgttcgcg tgcccgggga cttcaacctc acgctgctcg accacctgat cgccgagccc ggcctgctcg tcggctgctg taacgagctc aacgccgggt acgccgccga cggctacgcg cggtcgcggg gcgtcggcgc ctgcgccgtc acgttcaccg tcggcggact cagcgtgctc aacgccatcg ccggcgcgta cagcgagaac ctgccggtca tctgcatcgc cggagggccg aactccaacg actacggcac taaccgcatc ctccaccaca ccatcggcct cccggacttc tcccaggagc tccgctgctt ccagaccgtc acttgcaccc aggtacgtgt cccccctct gctcctcctc ggatttcccc ctaatttctt gggttgcaga tttgttggaa tcgatcgatq gtttgctaat gtttgtggat tcaggcggtg gtgaccaatc tggaggatgc gcacgagcag atcgacaccg ccatcgcgac ggcgctgcgg gagagcaagc ctgtgtacct cagcatcagc tgcaatctcc caqggctgcc tcaccccacg tttagccgcg accccgtccc cttcttcctc gccccaggt acccctctcc gttttatcat gaagcttatc ccataatcta ccaattttgt catgccatgt ctcgattcaa gagagtagga ttttatttac cccaaaaagg acgcctggtt gaattataag tattgagatc gtgcatattt gatacagtac cggaagttgt ctgatgattt caatatgttg taatatttca cttcagttcg atgctataag attggttgta ccaatgcatt tcagattttt gattcgatgc tatgaaattg gttgtaccat tgcatttcag attttcagtt tgtctgatga aattgtggca ttgcaggttg agtaacaaga tgggtctgga ggctgcggtg gaggccactg tcgagttcct gaacaaggcg gtgaagccgg tgctcgttgg cggccccaag ctgcgtgtgg caaaggcagg gaaggccttc gtcgaccttg ttgatgccag tggctacccc tacgcggtga tgccgtcggc caaggggctc gtgccggaga cgcacccccca cttcatcggc acctactggg gtgcggtcag
```

-continued

```
cacggccttc tgtgccgaga tcgtcgagtc ggccgacgcc tacctcttcg cagggccaat cttcaatgac tacagctctg tcggctactc cttcctcctc aagaaggaca aggccataat tgtgcaaccg gagcgtgtca tcgtcgggaa tggcccggcg tttgggtgcg tcatgatgaa ggagttctta tctgagctgg ctaagcgcgt caacaagaac accactgctt acgagaacta caagaggatc ttcgtcctga gggccagcgc tggagaggag ccgaatgagc cgctgcgcgt caatgtgctc ttcaagcacg tccagaagat gctgaacagt gacagtgctg tgattgccga gactggtgac tcctggttca attgccagaa gctgaagctc cctgagggct gcgggtgagc attctgaaac ttgctacaac cctgttgtga atggttttac aatgttcttg gtgaatatac tgagtggttt attgcatgct gcaggtatga attccaaatg cagtatggtt ccattggatg gtcagtgggt gcattgctcg gatatgctca gggcgctaag gacaagcgtg tgattgcctg tattggtgat gggagtttcc aggtgaagca ccgtgatcac ttgatctttt gatcagatat gttgctaata tgatggcatg ttactgatgt gtgatcgtgg taatttcctg caggtgacgg cacaggatgt gtcaacaatg attcgctgtg cacagaacag cataatcttc ctgatcaaca acggcgggta caccattgag gtggagatcc atgacggtcc atacaacgtc atcaagaact ggaactacac tggtcttgtg gatgccatcc acaatggaga gggcaaatgc tggacttcta aggtatgcta actcttcgat cacctgacat tcaccacacg aggcttagac cgcagatgct cctatatctg aggaactgtt gctgatggtt gccatgatgt acattgcgca ggtgaagtgc gaggaggagc tgacggaggc gatcgggatg gcgctggggg agaagaagga ctgcctgtgc ttcattgagg tgatcgcgca caaggacgac accagcaaag agctgctgga atggggatcg agggtttctg ctgccaactc caggccacca aatcctcagt agaaacttt t agtacttagt tgcaagctgg gctcaatcat aataatgtaa acactttgcc cttcagttat gttccttgtg tccattccct cgggtttctg ttcttccagt tcggtagct ctgtatctac ttgtgaacat ctgtttctcc aatcaaatgc tacgagggtt atgagaggtt ttcagcttgc atccaactgt ttgattttgt gttgccatct gctacccggc acttggtaac gatttgatga gagcatggcc ggccagtgaa tcctgtgatc tgtgcgagat ccgtcacttg gaggcaggct actattgcat ggtcctcctc ccgtgagccg ttacttgtct ctgtctgcaa gaaatggcg atgaaattca gaagcgctag atcggtgtca acagggcaat aatctggtac ttcctccgtc tcaaaataaa tatagtttta cactattcac gtttacattt gaccgtttgt cttatttaaa tttatttta tgattagtat ttttattact attaggacta aatattttt aattttcat aaatttttta aataagacga tggcaaatgt taggcacgaa tatcataatg tagaagatat tcgcgatatt agagag
```

SEQ ID NO: 1 is the nucleotide sequence of the rice pdc2 gene. The start and end of the cDNA clone, pRcpdc2 are at nucleotide positions 2242 and 5070, respectively. The GenBank accession number for this sequence is U38199. The deduced amino acid sequence of the rice pdc2 gene is represented by SEQ ID NO: 3 as follows:

```
Met Glu Thr His Ile Gly Ser Val Asp Gly Ala Ala Ala Ala Ala Asp
Asn Gly Ala Val Gly Cys Pro Ala Ser Ala Val Gly Cys Pro Met Thr
Ser Ala Arg Pro Gly Val Ser Ala Arg Arg Gly Val Ala Gly Thr Ala
Pro Gly Glu Ala Ala Gly Ala Gly Gly Arg Gln Arg Arg Val Arg Val
Pro Gly Asp Phe Asn Leu Thr Leu Leu Asp His Leu Ile Ala Glu Pro
```

-continued

Gly Leu Leu Val Gly Cys Cys Asn Glu Leu Asn Ala Gly Tyr Ala Ala
Asp Gly Tyr Ala Arg Ser Arg Gly Val Gly Ala Cys Ala Val Thr Phe
Thr Val Gly Gly Leu Ser Val Leu Asn Ala Ile Ala Gly Ala Tyr Ser
Glu Asn Leu Pro Val Ile Cys Ile Ala Gly Gly Pro Asn Ser Asn Asp
Tyr Gly Thr Asn Arg Ile Leu Mis His Thr Ile Gly Leu Pro Asp Phe
Ser Gln Glu Leu Arg Cys Phe Gln Thr Val Thr Cys Thr Gln Ala Val
Val Thr Asn Leu Glu Asp Ala Ris Glu Gln Ile Asp Thr Ala Ile Ala
Thr Ala Leu Arg Glu Ser Lys Pro Val Tyr Leu Ser Ile Ser Cys Asn
Leu Pro Gly Leu Pro His Pro Thr Phe Ser Arg Asp Pro Val Pro Phe
Phe Leu Ala Pro Arg Leu Ser Asn Lys Met Gly Leu Glu Ala Ala Val
Glu Ala Thr Val Glu Phe Leu Asn Lys Ala Val Lys Pro Val Leu Val
Gly Gly Pro Lys Leu Arg Val Ala Lys Ala Gly Lys Ala Phe Val Asp
Leu Val Asp Ala Ser Gly Tyr Pro Tyr Ala Val Met Pro Ser Ala Lys
Gly Leu Val Pro Glu Thr His Pro His Phe Ile Gly Thr Tyr Trp Gly
Ala Val Ser Thr Ala Phe Cys Ala Glu Ile Val Glu Ser Ala Asp Ala
Tyr Leu Phe Ala Gly Pro Ile Phe Asn Asp Tyr Ser Ser Val Gly Tyr
Ser Phe Leu Leu Lys Lys Asp Lys Ala Ile Ile Val Gln Pro Glu Arg
Val Ile Val Gly Asn Gly Pro Ala Phe Gly Cys Val Met Met Lys Glu
Phe Leu Ser Glu Leu Ala Lys Arg Val Asn Lys Asn Thr Thr Ala Tyr
Glu Asn Tyr Lys Arg Ile Phe Val Leu Arg Ala Ser Ala Gly Glu Glu
Pro Asn Glu Pro Leu Arg Val Asn Val Leu Phe Lys His Val Gln Lys
Met Leu Asn Ser Asp Ser Ala Val Ile Ala Glu Thr Gly Asp Ser Trp
Phe Asn Cys Gln Lys Leu Lys Leu Pro Glu Gly Cys Gly Tyr Glu Phe
Gln Met Gln Tyr Gly Ser Ile Gly Trp Ser Val Gly Ala Leu Leu Gly
Tyr Ala Gln Gly Ala Lys Asp Lys Arg Val Ile Ala Cys Ile Gly Asp
Gly Ser Phe Gln Val Thr Ala Gln Asp Val Ser Thr Met Ile Arg Cys
Ala Gln Asn Ser Ile Ile Phe Leu Ile Asn Asn Gly Gly Tyr Thr Ile
Glu Val Glu Ile His Asp Gly Fro Tyr Asn Val Ile Lys Asn Trp Asn
Tyr Thr Gly Leu Val Asp Ala Ile His Asn Gly Glu Gly Lys Cys Trp
Thr Ser Lys Val Lys Cys Glu Glu Glu Leu Thr Glu Ala Ile Gly Met
Ala Leu Gly Glu Lys Lys Asp Cys Leu Cys Phe Ile Glu Val Ile Ala
His Lys Asp Asp Thr Ser Lys Glu Leu Leu Glu Trp Gly Ser Arg Val
Ser Ala Ala Asn Ser Arg Pro Pro Asn Pro Gln Glx

The present invention is directed to a nucleic acid sequence that encodes a regulatory element that can be operably linked to a gene sequence to regulate the expression of that gene. More particularly the regulatory sequence of SEQ ID NO: 2 induces the expression of linked genes upon exposure of cells containing such nucleic acid sequences to hypoxic conditions. The regulatory sequence of SEQ ID NO: 2 is virtually silent during normal levels of oxygen in cells, however as the oxygen level drops in the cells, the promoter becomes activated. Accordingly, the hypoxia inducible promoter can be used for up-regulating genes in any organism or tissue that is exposed to anaerobic or hypoxic conditions.

In one embodiment an expression vector is provided comprising a hypoxia inducible promoter, having a consecutive 20 base pair sequence identical to a consecutive 20 base pair portion of the sequence of SEQ ID NO: 2 located adjacent to a polylinker region. In one embodiment the promoter utilized is the nucleic acid sequence of SEQ ID NO: 2. The polylinker region of the expression vector simplifies the insertion of a preselected gene into the vector and operably links the gene to the hypoxia inducible promoter. The expression vector also typically includes a selectable marker gene or a visible marker gene to allow identification of plant or animal cells transformed with the exogenous DNA sequence. In one embodiment the expression vector further includes a prokaryotic selectable marker gene and a prokaryotic origin of replication that allows for the transformation and reproduction of the expression vector in prokaryotes. These transformed bacterial cells can be cultured to produce large quantities of the plasmid DNA. The specific transformation construct can then be isolated using techniques well known to those familiar with the art.

In accordance with the present invention a DNA construct comprising the regulatory element of SEQ ID NO: 2, a core promoter and a protein coding sequence operably linked to the core promoter is used to transform a plant cell, using procedures known to those familiar with the art. Such transformation procedures include but are not limited to microinjection, microprojectile bombardment, electroporation, calcium chloride permeabilization, polyethylene glycol permeabilization, protoplast fusion or bacterial mediated mechanisms such as Agrobacterium tumefaciens or Agrobacterium rhizogenes.

In one embodiment a transgenic plant entity is provided wherein the plant entity consists essentially of a plant cell, seed or plant produced from the in vitro introduction of an exogenous nucleic acid construct, comprising a hypoxia inducible promoter having a consecutive 20 base pair sequence identical to a consecutive 20 base pair portion of the sequence of SEQ ID NO: 2, into a plant cell. In one embodiment the exogenous nucleic acid construct further comprises a gene sequence operably linked to the hypoxia inducible promoter. The exogenous nucleic acid construct used to produce the transgenic plants in accordance with the present invention typically include a selectable marker gene or a visible marker gene to allow identification of the cells transformed with the exogenous DNA sequence.

An entire plant can be generated from a single transformed plant cell through cell culturing techniques known to those skilled in the art. Transformed cells (those containing the DNA inserted into the host cell's DNA) are selected from untransformed cells through the use of a selectable marker included as part of the introduced DNA sequences. Transformed cells/plant entities can also be identified by the expression of a visible marker included as part of the introduced DNA sequences. Visible markers include genes that impart a visible phenotypic trait such as seed color (i.e., yellow, purple or white genes) or shape (i.e., shrunken or plump genes). Selectable markers include genes that provide antibiotic resistance or herbicide resistance. Cells containing selectable marker genes are capable of surviving in the presence of antibiotic or herbicide concentrations that kill untransformed cells. Examples of selectable marker genes include the bar gene which provides resistance to the herbicide Basta, the nptII gene which confers kanamycin resistance and the hpt gene which confers hygromycin resistance.

In one embodiment the hypoxia inducible promoter of the present invention is used to generate transgenic plants that maintain plant energy levels under flooded conditions. For example, the hypoxia inducible promoter can be operably linked to key enzymes of the glycolytic pathway and these constructs can be used to produce transgenic plants that are more tolerant of anaerobic conditions. As noted above, switching energy production from aerobic glycolysis to anaerobic fermentation is one of the major metabolic adaptations plants undertake when they are submerged or confronted with a lack of oxygen. It is anticipated that placing at least a subset of the glycolytic enzymes under the control of a hypoxia inducible promoter will enhance the plant's tolerance of anaerobic conditions.

In one embodiment the hypoxia inducible promoter of the present invention is operably linked to exogenous genes and used to transform plant species other than rice to further enhance the expression of gene products that are normally induced under hypoxia conditions. The use of the rice exogenous promoter will avoid the disadvantages caused by co-suppression when plant cells are transformed with multiple copies of endogenous regulatory sequences driving the expression of genes.

In one embodiment the hypoxia inducible promoter of the present invention is used to express gene products in mammalian cells. In particular the promoter can be operably linked to genes that express a protein product that is effective against solid tumors (i.e., an anti-tumor agent). Solid tumors have proven difficult to treat with chemotherapy because the center of the tumors are frequently inadequately supplied or have poorly developed vasculature. As a result regions of solid tumors develop hypoxia. Despite the low oxygen levels tumor cells in a hypoxic environment do exhibit cellular activity. The hypoxia inducible promoter of the present invention can be operably linked to one or more genes that encode conventional anti-tumor therapeutics known to those skilled in the art. The construct can then be administered to a patient having a solid tumor, wherein the therapeutic gene product will only be expressed in cells exposed to a hypoxic environment (i.e. within the hypoxic regions of the solid tumor). In this manner the expression of the therapeutic gene product can be targeted to the cells of the solid tumor. In accordance with one embodiment the therapeutic agent comprises a protein that is toxic to cells.

To further enhance the targeted delivery of anti-tumor gene products to the cells of solid tumors, the DNA constructs can be directly injected into the solid tumor. Alternatively the DNA constructs can be conjugated/linked to various ligands or targeting moieties that have an affinity for tumor cells or are preferentially internalized by tumor cells (for example antibodies raised against tumor cells or ligands that bind to receptors that are only present in tumor cells or at least are more prevalent in tumor cells). In one embodiment the DNA constructs are encapsulated in a carrier that is linked to various ligands or targeting moieties that have an affinity for tumor cells. For example the carrier can be a collagen matrix, a hydrogel or liposomal carrier.

EXAMPLES

Materials and Methods

Screening of the Genomic Library and Construction of a Restriction Map of the pdc2 Gene An IR54 genomic library constructed in lambda GEM 11 vector (McGee 1995) was screened with the following probes generated from the plasmid pBGS-PDC containing maize pdc cDNA: a Bgl II-BamH I fragment of 702 bp representing the 5' end of the gene; a Kpn I-Hind III fragment of 607 bp spanning the middle; and a Hind III-EcoR I fragment of 366 bp of the 3' pdc coding region. Identification of the hybridizing clones and subsequent plaque purifications were carried out using standard procedures and phage DNA isolation was done using a liquid culture method. A pdc2-specific probe was made from the 3'-untranslated region of the maize pdc2 cDNA and was used to identify the rice pdc2 gene. Phage DNAs were digested with different restriction enzymes, electrophoresed on 0.9% agarose gel, and was hybridized with three different probes (5', 3' and middle region) after Southern blotting. The size of the bands was calculated by comparing with the rate of migration of a 1 kb ladder (Life Technologies) run on the same gel, and a restriction map of the positive phage clone, 2B, was constructed.

Cloning and Sequencing of the Rice pdc2 Gene

The rice pdc2 gene was subcloned into plasmid vector pGEM7Zf(+) (Promega) as three fragments from the positive phage clone 2B: a 2.4 kb Nsi I-BamH I fragment representing most of the 5'-upstream region, a 1 kb BamH I-Nsi I fragment representing the middle region, and a 2.5 kb fragment containing approximately 1.8 kb of the 3'-coding and untranslated regions. The inserted pdc fragments were serially deleted by exonuclease M using the Erase-a-Base protocol of Promega. Both strands of the deleted clones were sequenced by the dideoxy chain termination procedure using Sequenase version 2 protocol (United States Biochemicals). When required, synthetic oligonucleotides (19-mers) were used as primers for further sequencing. In some cases compressions were resolved by performing the reactions at 70° C. using Taq DNA polymerase (United States Biochemicals) and using the deaza-GTP analog. DNA sequences were analyzed using the University of Wisconsin Genetics Computer Group (GCG) package (Devereux et al. 1984) and the DNA Strider program (Marck 1988).

Isolation of Total RNA

Two-week-old uniform seedlings of rice (IR54 variety) were transferred to two liter flasks and subjected to anaerobic conditions. Seedlings were submerged in distilled water through which nitrogen gas was continuously bubbled. The anaerobic treatment was conducted in the dark at 25° C. Control seedlings were maintained in the dark at 25° C. Tissues were harvested and immersed in liquid nitrogen. Extraction of RNA was carried out according to the procedure of Logmann et al. (Anal Biochem 163: 16–20, 1987) with modifications. The frozen tissue (2 gm) was ground in liquid nitrogen in an autoclaved mortar and pestle, and transferred to autoclaved plastic centrifuge tubes. Extraction buffer (4M guanidine hydrochloride, 20 mM MES, 20 mM EDTA, 4 ml/g tissue) was added to each tube. After vigorous shaking and complete mixing the suspension was extracted once with phenol:chloroform:isoamyl alcohol (25:24:1) and centrifuged for 45 minutes at room temperature at 10,000 rpm in a Beckman centrifuge using JA-20 rotor. Then 0.2 volumes of 1 M acetic acid [diethyl pyrocarbonate (DEPC) - treated] were added to the supernatant to acidify the contents, and the RNA was precipitated by adding 0.7 volumes of ethanol after 1 hour incubation at −80° C. following centrifugation at 10,000 rpm for 10 minutes. The RNA pellet was subsequently dissolved in DEPC-treated water and reprecipitated using ⅓ volume of 8 M LiCl (overnight at 4° C.). The RNA sample was subsequently washed with 80% ethanol and dissolved in DEPC-water after drying, and quantified spectrophotometrically. Suspension cultures of Radon variety were also treated in the same way under anaerobic conditions. Cycloheximide was added at a final concentration of 100 $\mu$M, and anaerobic conditions were applied for various time periods after 30 minutes pretreatment. RNA was isolated using the same procedure described above.

Synthesis of Antisense Probes

Gene-specific antisense RNA probes were synthesized for use in ribonuclease protection assays using the Maxiscript II System (Ambion). pdc1 (Hossain et al. Plant Physiol 106: 799–800, 1994), pdc2 (Huq et al. Plant Physiol 109: 722, 1995), and ubi1 (Huq et al. Plant Physiol 113: 305, 1997) cDNAs were all subcloned into pSPORT1 plasmid vector (Life Technologies) as EcoRI-Not 1 fragments. pdc1 was linearized with Xho 1, pdc2 with Sca I, and ubi1 with Nco I. These linearized plasmids were transcribed with SP6 RNA polymerase to produce gene-specific antisense RNA probes from the 3'-untranslated regions. Transcription reactions were performed in 20 $\mu$l volume containing 1 $\mu$g linearized DNA template; 1×transcription buffer; 0.5 mM ATP; 0.5 mM GTP; 0.5 mM UTP; 10 units SP6 RNA polymerase; and 3.5 $\mu$M [$\alpha$-$^{32}$P]CTP (800 Ci/mmole, 20 mCi/ml) and incubated for 1 hr at 37° C. Reaction conditions for the antisense rice ubiquitin 1 cDNA probe were essentially the same as for the gene-specific probes. Following transcription, all reactions were treated with RNase-free DNase I (0.4 units/$\mu$l , Ambion) for 15 min at 37° C. to remove contaminating template DNA. Full-length probes were purified from 5% denaturing polyacrylamide gels.

Ribonuclease Protection Assays

Ribonuclease protection assays (RPAs) were performed using total RNA isolated from shoots and roots of two-week-old IR54 variety treated under anaerobic conditions for 0, 1.5, 3, 6, 12, 24, 48, and 72 hours time periods. Assays were carried out using the RPAII System (Ambion) according to the protocol supplied by the company. Five $\mu$g total RNA samples of each time point were hybridized with 2–4×10$^4$ CPM of high-specific activity (typically 6 to 7×10$^8$ cpm/$\mu$g) antisense probes specific for either pdc2 or pdc1 gene. A rice ubi 1 cDNA isolated from IR54 variety was used as an internal control to show the amount of RNA used. Ribonuclease digestions were performed using 1:100 dilutions of the supplied ribonuclease cocktail (final concentration=0.2 units/ml RNase A; 2.0 units/ml RNase T1). Following RNase treatment, total samples were subjected to electrophoresis through 5% denaturing polyacrylamide gels, wrapped in plastic wrap, and exposed to X-ray film with intensifying screen for autoradiography. The expected sizes of the full-length and protected fragments using the various gene-specific probes were as follows: 343 and 286, respectively for pdc1; 235 and 178; respectively for pdc 2; 300 and 243, respectively for rice ubi 1 (internal control).

Northern Blot Analyses

Ten $\mu$g of total RNA isolated from suspension cells (Radon variety) was loaded in each lane and was resolved in 1.2% formaldehyde-agarose gel according to standard procedures. RNA was transferred to nitrocellulose filters by capillary action and probed with a radiolabeled 700 bp probe made from the 3'-region of the pdc2 gene. This probe has an ca. 500 bp region that is homologous to all the pdc genes. Prehybridization and hybridization reactions were carried out at 65° C. Filters were washed according to the instructions of the suppliers (Amersham). A 28S rDNA probe was used as a control to show the amount of RNA loaded in each lane. This blot was washed finally with 0.05×SSC and 0.1% SDS at 65° C. twice and autoradiographed for 4 hours.

Construction of PDC Protein Similarity Tree

The deduced amino acid sequences of five pdc genes were compared using the GAP program of the GCG Sequence Analysis Software Package, Version 7.3 (Genetics Computer Group, Madison, Wis., USA). The pdc genes were described previously as rice pdc 1 (GenBank Accession Number U07338), rice pdc2 (GenBank Accession Number U27350), rice pdc3 (GenBank Accession Number UO7339), maize pdc1 (GenBank Accession Number X5946), Yeast pdc (GenBank Accession Number X77316), and bacterial pdc (GenBank Accession Number X59558).

RFLP Mapping

A mapping population consisting of 113 backcross (BC) individuals derived from the cross O.sativa/O.longistaminata/O.sativa was maintained at Cornell University and was used to place pdc 1, pdc2, and pdc3 on to rice chromosome maps. DNA from the indica recurrent parent (BS 125) and the interspecific Fl (BS 125/WL02) was digested with six restriction enzymes (EcoRV, Hind III, Xba I, Sca I, Dra 1, EcoR I), electrophoresed overnight on 0.9% agarose gels, and blotted onto Hybond N+ (Amersharn. Corp.) according to the manufacturer's instructions for use in parental polymorphism surveys. For mapping purposes, DNA from 113 backcross progeny was digested and blotted using the same procedures.

The following were used as probes: 1a.) pdc1—a 2.2 kb cDNA in pSPORT 1 vector (Life Technologies) that contained an open reading frame for the Pdc 1 gene which is highly homologous to the other pdc genes and is not specific for pdc 1 gene (hereafter referred to as clone 1A), lb.) pdc 1—a 115 bp Mlu I-Nco 1 fragment of the 5' untranslated region specific for pdc 1 gene (hereafter referred to as clone 1B), 2a.) pdc2—a 700 bp 3' fragment of the pdc2c DNA in pSPORT1 vector (Life Technologies) (hereafter referred to as clone 2A), 2b.) pdc2—a 200 bp Sca I-Not I fragment from the 3'-untranslated region specific for pdc2 gene (hereafter referred to as clone 2B), and 3.) pdc3—a 2.8 kb 5' fragment of the pdc3 gene in pUC19 (Life Technologies) (hereafter referred to as clone 3). The fragments were labeled with $^{32}$P using the random hexamer method and used as probes in Southern analyses. Filters were hybridized overnight at 65° C. and washed 3 times for 20 minutes each at 65° C. at successive stringencies of 2×, 1×, and 0.5×SSC (with 0.1% SDS) (I×SSC is 0.15M NaCl, 0.015M sodium citrate). Labeled filters were exposed to X-ray film with intensifying screen for 5 days at −80° C. For mapping, segregation in the backcross progeny was scored by the presence or absence of the polymorphic band coming from *O.longistaminanta*. Linkage analysis was performed using Mapmaker version 2.0 on a Macintosh Performa 475. Genetic distance is expressed in Kosambi cM (Kosambi, Ann. Eugenet. 12:172–175, 1944) and the map was constructed using a LOD 2.0 significance threshold.

Results

Isolation and Sequence Analyses of the pdc2 Gene

Two probes from the maize pdc cDNA were used to screen an IR54 rice genomic library, and eighteen positive clones that hybridized to both the 5'- and 3'-regions of the maize pdc cDNA were identified. Eight of these 18 clones were found to be pdc3 and 2 of them were found to be pdc 1. Two clones, 2B and 14C, were similar in restriction pattern and hybridized to a pdc2-specific probe. The 2B phage clone was selected for further subcloning and sequencing. In order to subclone the pdc2 gene, a partial restriction map of the phage clone was constructed using different restriction endonucleases. The restriction map is shown in FIG. 1, and the region that hybridized to the 5'- and 3'-region probes is shown in larger scale. The 5.9 kb fragment that is shown in larger scale was subcloned as 3 fragments and was sequenced from both ends. The vector containing pdc2 gene was called pRgpdc2. The nucleotide and predicted amino acid sequences of the rice pdc2 gene, including approximately 2.38 kb upstream region of the translational start site, is shown as (SEQ ID NO: 2) and (SEQ ID NO: 3), respectively. The sequence of the coding region exactly matched with the sequence of the previously isolated pdc 2 cDNA including the 5'- and 3'-untranslated regions. It has an open-reading-frame of 1812 nucleotides that encodes a 603 amino acid residue polypeptide with molecular mass of 64 kD. The sequence also revealed that there were five intervening introns present in the coding region.

Ribonuclease Protection Assays

Ribonuclease protection assays (RPAs) were performed to determine the spatial and temporal expression patterns of the pdc2 and pdc1 genes. RPAs using pdc2-specific probe showed that an ca. 170 bp fragment is protected which is close to the expected size (178 bp) for the pdc2-specific messages. The results also showed that this gene is highly induced within 1.5 hours of anoxia in both shoots and roots of IR54 rice variety. The induction is higher in shoots than that in roots. The message levels peaked around 3 hours of anoxia and then gradually decreased with time of anoxia in both shoots and roots. The rice ubi 1 gene has been found not to be induced under anoxia. So, the ubi1 gene-specific probe was used as an internal control to show the amount of RNA used in each sample. The ubi 1 message levels showed that a little higher amount of RNA was used in the 3 hour shoot sample, and the 24 hour root sample was probably degraded.

A pdc 1 specific probe protected an approximately 280 bp fragment, which is close to the expected size (286 bp) for the pdc1-specific transcripts. The results showed that pdc 1 is also highly induced under anoxia, and that the induction is also more in shoots than in roots. The message levels peaked around 6 hours of anoxia and gradually decreased with time of anoxia in both shoots and roots. These results also showed that pdc2 was more induced during the early period of time (1.5 to 12 hours) than pdc 1 which was more induced during the later period of time (24 to 72 hours) under anoxia in both shoots and roots.

Northern Blot Analyses

Northern blots were performed on total RNA isolated from suspension cells treated under anaerobic conditions in the presence or absence of cycloheximide to test whether the induction of the pdc genes require synthesis of new proteins. A 100 $\mu$M final concentration of cycloheximide was found to reduce the induction of pdc genes under anaerobic conditions. This result indicated that the induction of pdc genes indeed requires new protein synthesis. The reduction in induction was more prominent in the 9-hour nitrogen treatment sample in the presence of cycloheximide. Alcohol dehydrogenase (Adh) gene from maize was used as a probe and the induction of this gene was also found to be downregulated by cycloheximide. However, cycloheximide in the presence of $O_2$, induced Adh transcripts.

Evolutionary Relationship of the pdc Genes

The intron lengths and intron positions are compared among rice pdc 1 and 2, and maize pdc1 genes. Rice pdc's have five introns, whereas maize pdc1 has only three introns. The length of the first intron in both the rice pdc 1 and 2 genes are more conserved than the other 4 introns. The lengths of the three maize introns are not consistent with the corresponding introns of the rice pdc 1 and 2 genes. However, the positions of the corresponding introns are highly conserved in the deduced amino acid sequences among rice pdc 1 and 2, and maize pdc 1 genes.

A similarity-tree based on pairwise comparisons of PDC amino acid sequences was also constructed using the GCG PILEUP program. The plant PDCs were found to be closely related to each other. Rice PDC 1 was more closely related to maize PDC 1 and rice PDC 3 than to rice PDC2. The bacterial PDC was more similar to the plant PDCs than was the yeast PDC.

Mapping of the pdc Genes

The rice pdc 1 probe (1A) detected a multiple copy gene family with polymorphic fragments observed in EcoR V, Hind III, Dra I, Xba I and Sca I digested parental DNA. The probe was hybridized to Sca I digested DNA from the mapping population. Three scorable polymorphic fragments were seen that were estimated to be 25 kb, 7 kb, and 3 kb. To determine which of these fragments hybridized specifically to the pdc 1 gene, the pdc 1-specific probe, IB, was hybridized to DNA digested with the five enzymes mentioned above. In the Sca I digested DNA, only the 7 kb polymorphic fragment gave a hybridization signal. This band was mapped to rice chromosome 5 between CDO105 and CDO89. On mapping filters probed with clone 1A, the 7 kb fragment co-segregated with the 3 kb fragment in ScaI digested DNA. Both mapped to the same location on rice chromosome 5.

When the pdc2 clone (2A) was used as a probe on the same parental survey filters, a previously undetected 7.8 kb polymorphic fragment was detected using DraI digested DNA. To confirm that this fragment was specific to pdc2, clone 2B was used as a probe on the same parental survey filters. An identical hybridization pattern was observed. The 7.8 kb fragment was mapped to rice chromosome 3 between CDO260 and RG369A using DraI digested DNA from the BC population.

When pdc3 clone (3) was used to probe Sca1-digested DNA, a 25 kb polymorphic fragment was observed. This band was identical in molecular weight to that observed when the pdc 1 2.2 kb cDNA (clone 1A) was used as a probe. This band mapped to the bottom of rice chromosome 7 distal to RG351, suggesting that the pdc probes, IA and 3, detected the same 25 kb Sca I genomic fragment. Because the pdc 1-specific probe, 1B, did not detect this 25 kb band on Sca I-digested DNA, it may be concluded that this band is pdc3-specific.

Discussion

The isolation and characterization of two pdc genes and two pdc cDNAs from rice has been previously reported. This investigation reports the isolation and characterization of another gene, called pdc2, from rice. The pdc2 gene has an open-reading-frame of 1812 nucleotides that presumably encodes a 603 amino-acid-residue polypeptide. The molecular weight of the deduced polypeptide is 64 kD. A 64 kD polypeptide was previously purified from rice along with a 62 kD polypeptide, and thus it was concluded that the PDC holoenzyme consisted of a tetramer of two different molecular weight polypeptides in rice. This provides evidence that the 64 kD deduced polypeptide encoded by the pdc2 gene might be a PDC polypeptide. Moreover, both the deduced amino acid and nucleotide sequences of this gene are highly homologous to that of the rice and maize pdc1 genes. Rice PDC2 is 88% similar and 78% identical to rice PDC 1, and 88% similar and 79% identical to maize PDC1 enzymes. The pdc2 gene also has five introns, as found in the pdc1 gene in rice. The exon-intron splice junctions conform to the consensus sequences found in plants. But, the translation initiation site of this gene does not conform to the consensus sequences for plant translational initiation sites or the Kozak consensus sequences. However several other plant genes have previously been identified that do not conform to the consensus plant translation initiated site.

The open-reading-frame of the pdc2 gene exactly matched with the previously isolated cDNA (pRcpdc2) including the 5'- and 3'-untranslated regions. Approximately 2.38 kb upstream of the translational start site (SEQ ID NO: 1) has been sequenced. A TATA-box-like sequence has been found from 2180 to 2186 nucleotides which is 65 nucleotides upstream of the start site of the pRcpdc2 cDNA. This suggests that the cDNA was near full-length and the sequence from 2180 to 2186 might be the actual TATA box. Moreover, this 2.38 kb region was fused to the uidA gene and the resulting construct showed GUS activity after being shot into rice suspension cells.

The 2.38 kb region has multiple copies of the GT- and GC-motif-like sequences and one G-box-like sequence (SEQ ID NO: 1). The GT and GC motifs whose core sequences are 5'-GGTTT-3' and 5'-GC(G/C)CC-3", respectively, are found in many anaerobically-inducible genes including the rice pdc 1 gene, and the G-box-like sequence has been found to be involved in altering expression by many different environmental stresses. These observations require further experimental evidences to confirm the exact role of these boxes in the pdc2 promoter.

The spatial and temporal expression patterns of the pdc2 and pdc1 genes were investigated by RNase protection assays (RPAs). The expression patterns showed that the pdc2 and pdc1 genes were highly induced in both shoots and roots. Moreover, pdc2 was more induced in both shoots and roots during the early time of anoxia (1.5 to 12 hours) than pdc1 gene which was induced slightly more during the later period of anoxia (24 to 72 hours). This was in contrast to previous results showing that the pdc1 gene was more inducible than pdc2 gene using the 5'- or 3'-untranslated region probes from the pdc1 or pdc2 gene, respectively, on Northern blots. Recently Rivoal et al. (1997) reported isolation of another partial cDNA called pdc4 which is 96 and 95% identical to pRcpdc 1 in nucleic acid and amino acid sequence, respectively. Since pdc 1 and pdc 4 are highly homologous, the hybridizing signals detected by the 5'-untranslated region probe in our previous report (Hossain et al. 1996) might represent the combined signal of pdc 1 and pdc4 genes which could not be distinguished on Northern blots even under stringent washing conditions. This observation was supported by Rivoal et al. (1997) as these authors also could not distinguish hybridization between these two genes.

Since RPAs are very sensitive and more specific than Northern blots, this crosshybridization between pdc 1 and pdc 4 genes was eliminated and the more recent results represent only the induction of pdc1 gene. Using this analysis pdc2 has been found to be more inducible than the pdc 1 gene in both shoots and roots.

Cells were also treated with cycloheximide to investigate whether the induction of pdc genes requires synthesis of any new proteins. Cycloheximide at a concentration from 20 to 300 $\mu$M was found to reduce protein synthesis in rice suspension cells. Cells treated with 100 $\mu$M cycloheximide, under anaerobic conditions, had a reduced induction of both pdc and Adh genes. This result indicated that the induction of pdc as well as Adh requires synthesis of new proteins. Suspension culture cells are already under partial hypoxic conditions and high levels of pdc transcripts were found in the control sample ($O_2$ lane). This assay was performed using a common probe that detects all the pdc genes, because the RNA was isolated from a suspension cells of a variety of rice (Radon) that was different from the variety (IR54) that the gene-specific probes were isolated from, and the later might not have hybridized accurately.

Cycloheximide also induced Adh messages in the presence of $O_2$. This was not surprising because cycloheximide has also been found to induce other types of genes such as α-amylases 3 gene. This can be explained by the fact that one of the first effects of anoxia is to reduce translation to a great extent. The half-life of Adh transcripts are also increased under anoxia. Thus, the reduction of translation might trigger a mechanism to stabilize the Adh transcripts. The results also suggest that a protein factor(s) which is more stable under aerobic but unstable under anaerobic conditions was responsible for increased stability of Adh transcripts. The expression and stability of this factor(s) might also be regulated by anaerobic conditions. These hypotheses might account for the increased levels of Adh transcripts in the presence of cycloheximide under aerobic conditions, although cycloheximide induced transcription cannot be ruled out without further investigation.

The evolutionary relationship of the pdc genes was studied by comparing their intron positions, intron lengths, and by constructing a gene tree. Although intron lengths were found to be variable among rice pdc 1 and 2, and maize pdc 1 genes, the intron positions were found to be highly conserved among these three genes. This might indicate an evolutionary conservation of the functional domains or even the whole protein in rice and maize.

The evolutionary relationship among these genes has also been compared by constructing a PDC protein-similarity tree. As might be expected, the plant PDC's are closer to each other, however, rice pdc4 and maize pdc2 and pdc3 genes could not be compared because the complete nucleotide sequences were not available. Rice PDC 1 was more similar to maize PDC 1 than to the other rice PDC genes, and it was more similar to rice PDC3 than to rice PDC2.

The map locations of three pdc genes have been determined in the rice genome, and confirms the presence of the three independent pdc loci in rice. The use of gene-specific probes was essential for resolving the locations of each pdc gene. The co-segregation of the pdc 1-specific 7 kb band and the 3 kb band that hybridized only to probe 1A on the Sca I digested DNA suggested that there might be an additional member of this gene family in tandem array with the pdc I gene on chromosome 5.

The orthologous counterpart in maize to rice pdc 1 would be predicted to lie on either of two internally duplicated regions of maize chromosome 6 or 8, based on the alignment of comparative rice-maize maps. The maize pdc 1 locus has previously been mapped to maize chromosome 8 between umc 173 and umc 12. Thus, these two pdc 1 genes appear to represent homologues in the rice and the maize genomes. Branching out to other members of the Gramineae, an orthologous locus would be predicted to be located on oat linkage group A and on Triticeae chromosome 1.

Rice pdc2 mapped to rice chromosome 3 and the predicted orthologous locus in maize would be expected to lie on either maize chromosomes 1 or 9. However, a locus known as maize pdc2 has been mapped to maize chromosome 8 (within 40 cM of maize pdc 1) in a region that shows no evidence of conserved linkage with the markers near the pdc2 locus in rice. Therefore, there is no data to suggest that the maize pdc2 locus is orthologous to this newly mapped pdc2 locus in rice. It is possible that the maize pdc2 locus arose as a parologous counterpart to maize pdc1 (which is located nearby on the same chromosome). In this case, there would be no counterpart in the rice genome.

Rice pdc3 mapped to the distal portion of rice chromosome 7. Based on the placement of the closest linked marker mapped in both maize and rice (CDO38), the predicted orthologue in maize would be expected to lie on either maize chromosomes 1 or 7. It has been reported that maize pdc3 lies on maize chromosome 1; accordingly, it is believed that maize pdc3 is orthologous to rice pdc3.

What is claimed is:

1. An isolated polynucleotide having a sequence as set forth in SEQ ID NO: 2.

2. A plant expression vector comprising an hypoxia inducible promoter wherein the hypoxia inducible promoter comprises the nucleotide sequence set forth in SEQ ID NO: 2.

3. The plant expression vector of claim 2, further comprising a polylinker operably linked to the hypoxia inducible promoter.

4. The plant expression vector of claim 2, further comprising a coding sequence operably linked to the hypoxia inducible promoter, wherein the expression of the coding is regulated by the hypoxia inducible promoter.

5. The plant expression vector of claim 2, further comprising a selectable marker gene.

6. A plant expression vector comprising
    a rapid response hypoxia inducible promoter having a sequence identical to the sequence as set forth in SEQ ID NO: 2; and
    a polylinker operably linked to said hypoxia inducible promoter,
    wherein the rapid response hypoxia inducible promoter induces transcription within 12 hours of hypoxia.

7. The plant expression vector of claim 6, wherein the polylinker is also operably linked to a core promoter.

8. The plant expression vector of claim 6, further comprising a coding sequence operably linked to the rapid response hypoxia inducible promoter, wherein the expression of the coding is regulated by the rapid response hypoxia inducible promoter.

9. The plant expression vector of claim 6, further comprising a selectable marker gene.

10. The plant expression vector of claim 6, further comprising nucleic acid sequences that enable replication of the expression vector in a bacterial host, and a gene encoding a selectable marker for selecting transformed cells.

11. The expression vector of claim 6, wherein the rapid response hypoxia inducible promoter induces transcription within 6 hours of hypoxia.

12. The expression vector of claim 11, wherein the rapid response hypoxia inducible promoter induces transcription within 1.5 hours of hypoxia.

* * * * *